United States Patent [19]

Messing et al.

[11] 4,286,061

[45] Aug. 25, 1981

[54] METHOD FOR CONTINUOUS CULTURING OF MICROBES

[75] Inventors: Ralph A. Messing, Horseheads; Robert A. Oppermann, Painted Post; Lynn B. Simpson, Corning; Milton M. Takeguchi, Big Flats, all of N.Y.

[73] Assignee: Corning Glass Works, Corning, N.Y.

[21] Appl. No.: 162,582

[22] Filed: Jun. 23, 1980

Related U.S. Application Data

[63] Continuation-in-part of Ser. No. 939,190, Sep. 5, 1978, abandoned.

[51] Int. Cl.$^3$ ............................................. C12N 11/14
[52] U.S. Cl. .................................. 435/176; 435/813; 435/839; 435/842; 435/849; 435/850; 435/871; 435/942
[58] Field of Search ............... 435/176, 253, 254, 255, 435/813

[56] References Cited

U.S. PATENT DOCUMENTS

| | | | |
|---|---|---|---|
| 1,833,716 | 11/1931 | Kluyver et al. | 435/148 |
| 1,937,672 | 12/1933 | Sherman | 435/141 |
| 3,402,103 | 9/1968 | Amberg et al. | 435/842 X |
| 4,009,286 | 2/1977 | Moll et al. | 435/176 X |

FOREIGN PATENT DOCUMENTS 1519200 7/1978 United Kingdom .

OTHER PUBLICATIONS

Norris, J. R. et al., "Methods in Microbiology", vol. 2 Academic Press Inc., London, 1970, pp. 259–276 & 349–376.
Mateles, R. I. et al., "Measurement of Unsteady State Growth Rates of Microorganisms", Nature, 208, 1965, pp. 263–265.

*Primary Examiner*—Robert A. Yoncoskie
*Attorney, Agent, or Firm*—William E. Maycock

[57] ABSTRACT

A method for the continuous culturing of microbes in a plug-flow reactor which comprises the steps of:

A. supplying medium to microbes immobilized on a porous inorganic support at a rate sufficient to maintain such microbes substantially in a logarithmic growth state and B. removing microbe-containing effluent from the immobilized microbes at a rate equal to the medium supply rate, wherein the microbes are selected from the group consisting of bacteria, yeasts, and fungus-like organisms; such reactor is operated continuously in a substantially plug-flow mode; the immobilized microbes are substantially covered by said medium; and such porous inorganic support has a controlled porosity such that at least 70% of the pores, on a pore size distribution basis, have a pore diameter, a. in the case of bacteria, at least as large as the smallest major dimension of the microbes but less than about five times the largest major dimension of the microbes;

b. in the case of yeasts, at least as large as the smallest dimension of the microbes but less than about four times the largest dimension of the microbes; and c. in the case of fungus-like organisms, at least as large as the smallest major dimension of the microbes but less than about sixteen times the largest major dimension of the microbes.

10 Claims, No Drawings

METHOD FOR CONTINUOUS CULTURING OF MICROBES

The present application is a continuation-in-part of application Ser. No. 939,190, filed Sept. 5, 1978, now abandoned.

CROSS-REFERENCES TO RELATED APPLICATIONS

Patent Application Ser. No. 833,278, filed Sept. 14, 1977 in the names of Ralph A. Messing and Robert A. Oppermann and entitled, "High Surface Low Volume Biomass Composite", now U.S. Pat. No.4,153,510; Patent Application Ser. No. 833,277, filed Sept. 14, 1977 in the names of Ralph A. Messing and Robert A. Oppermann and entitled, "High Surface Low Volume Yeast Biomass Composite", abandoned in favor of a continuation-in-part application, Ser. No. 918,794, filed June 26, 1978, now U.S. Pat. No. 4,149,937; and Patent Application Ser. No. 833,275, filed Sept. 14, 1977 in the names of Ralph A. Messing and Robert A. Oppermann and entitled, "High Surface Low Volume Fungal Biomass Composite", abandoned in favor of a continuation-in-part application, Ser. No. 918,928, filed June 26, 1978, now U.S. Pat. No. 4,149,936.

BACKGROUND OF THE INVENTION

The continuous culturing of microbes (i.e., microorganisms) is, in principle, well known for the production of large quantities of microbes, both as a research tool and for the preparation or isolation of microbial products. Thus, such continuous culturing is useful for general research purposes, such as the isolation of such cellular components as enzymes, cell walls, cytochromes, and the like; as a source of microorganisms for industrial biochemical processes, such as the production of fermented beverages, antibiotics, alcohol, organic carboxylic acids, cheeses, and the like; for the production of single-cell protein as an animal feed supplement; and for the production of bacterial vaccines, to name but a few examples.

In the past, the continuous culturing of microbes most often has utilized either the chemostat or the turbidostat. See, e.g., J. R. Norris and D. W. Ribbons, Editors, "Methods in Microbiology", Vol. 2, Academic Press Inc. (London) Ltd., London, 1970, pp. 259-276 and 349-376.

In the chemostat, a culture of fixed volume is contained in a suitably-constructed vessel to which medium is pumped at a constant rate. Typically, constant culture volume is achieved by employing a vessel which has a constant level overflow device. The medium is compounded to contain an excess of all substances essential for maximum microbial growth, except for one which is present in a growth-limiting amount. As a consequence, the culture can grow only at a rate which is directly proportional to the medium flow rate.

The turbidostat is a continuous-culture apparatus in which a photoelectric monitor detects deviations from some pre-selected culture turbidity (i.e., constant microbial population density) and passes a signal calling for a compensatory increase or decrease in dilution rate to a pump or valve controlling the flow of growth medium. Apart from the photoelectric control system and some simple optical requirements with respect to the culture vessel, all of the components of a turbidostat have functions similar to those of a chemostat.

In practice, both the chemostat and the turbidostat are designed to utilize microbial specific growth rates of less than about one-half the maximum specific growth rate. Furthermore, both devices are subject to wash-out which occurs when the rate of dilution (i.e., medium flow rate) is increased beyond the culture growth rate. Because there is a significant lag in the adjustment of growth rate to dilution, such lag and the problems associated with wash-out must be taken into account in continuous culture systems. See, e.g., R. I. Mateless et al., *Nature*, 208, 263 (1965).

SUMMARY OF THE INVENTION

It is therefore an object of the present invention to provide a method for the continuous culturing of microbes which is not subject to wash-out.

It also is an object of the present invention to provide a method for the continuous culturing of microbes which takes advantage of microbe maximum specific growth rates.

These and other objects will be apparent to one having ordinary skill in the art from the consideration of the specification and claims which follow.

Accordingly, the present invention provides a method for the continuous culturing of microbes in a plug-flow reactor which comprises the steps of:

A. supplying medium to microbes immobilized on a porous inorganic support at a rate sufficient to maintain such microbes substantially in a logarithmic growth state and B. removing microbe-containing effluent from the immobilized microbes at a rate equal to the medium supply rate, wherein the microbes are selected from the group consisting of bacteria, yeasts, and fungus-like organisms; such reactor is operated continuously in a substantially plug-flow mode; the immobilized microbes are substantially covered by said medium; and such porous inorganic support has a controlled porosity such that at least 70% of the pores, on a pore size distribution basis, have a pore diameter, a. in the case of bacteria, at least as large as the smallest major dimension of the microbes but less than about five times the largest major dimension of the microbes;

b. in the case of yeasts, at least as large as the smallest dimension of the microbes but less than about four times the largest dimension of the microbes; and c. in the case of fungus-like organisms, at least as large as the smallest major dimension of the microbes but less than about sixteen times the largest major dimension of the microbes.

DETAILED DESCRIPTION OF THE INVENTION

The microbes which can be employed in the present invention in general are those microbes which are capable of being immobilized on an inorganic support. Thus, such microbes include bacteria, yeasts, fungi, and algae. The last two types of microbes are conveniently grouped together as fungus-like organisms, i.e., microbes which reproduce by spore formation and demonstrate mycelial growth. As used herein, the term "bacteria" is meant to include all microbes which reproduce by fission or simple division. Similarly, the term "yeasts" is meant to include all microbes which reproduce by budding. Bacteria and yeasts are preferred, with bacteria being most preferred, which bacteria can be aerobic or anaerobic.

The suitable inorganic supports in general are inorganic materials having available surface hydroxy or oxide groups. Such materials can be classified in terms of chemical composition as siliceous or nonsiliceous metal oxides. Siliceous supports include, among others, glass, colloidal silica, wollastonite, cordierite, dried silica gel, bentonite, and the like. Representative nonsiliceous metal oxides include alumina, hydroxy apatite, and nickel oxide. The siliceous materials are preferred, with cordierite materials being most preferred.

The physical state of the inorganic support is not critical to the present invention. Thus, the support can be granular, large particles, or a shaped article.

In general, the microbes can be immobilized by any known means which can vary from simple adsorption to chemical coupling. Adsorption, of course, involves contacting an aqueous suspension of the microbes to be immobilized with the inorganic support for a time sufficient to permit the desired (or maximum) degree of immobilization. Chemical coupling typically involves treating the inorganic support with one or more chemical compounds, followed by contacting the treated support with an aqueous suspension of the microbes. Among the chemical compounds which can be used to treat the inorganic support are o-dianisidine (U.S. Pat. No. 3,983,000), polymeric isocyanates (U.S. Pat. No. 4,071,409), silanes (U.S. Pat. Nos. 3,519,538 and 3,652,761), and the like. See also U.S. Pat. Nos. 3,930,951 and 3,933,589.

It should be apparent to one having ordinary skill in the art that the means for retaining or confining the immobilized microbes and the means for supplying medium thereto and removing microbe-containing effluent therefrom are not critical. As a practical matter, however, the immobilized microbes most often will be contained in a columnar vessel. Obviously, the columnar vessel can be jacketed to permit carrying out the present invention at any desired temperature.

Once the immobilized microbes are charged to a suitable vessel, four conditions then must be imposed in order to carry out the method of the present invention.

First, the immobilized microbes must be substantially covered by the medium. This condition primarily is a consequence of the need to operate the immobilized microbe reactor in a plug-flow mode, as discussed hereinbelow. In general, no more than about ten percent of the immobilized microbes, on a volume basis, will not be covered by medium. Typically, however, no more than about five percent of the immobilized microbes will not be covered by medium. When using a columnar vessel in which the medium enters one end and exits from the other, the immobilized microbes will be in an essentially covered environment.

Second, medium is supplied to the immobilized microbes at a rate sufficient to maintain the microbes substantially in a logarithmic growth state. Such rate is readily determined by one having ordinary skill in the art who also can readily ascertain by known means whether or not the microbes are substantially in a logarithmic growth state. As used herein, the term "substantially" means only that at least about one-half of the microbial population is in a logarithmic growth state.

Third, the rate of supply of medium to the immobilized microbe reactor is the same as the rate of removal of microbe-containing effluent from the reactor. This condition, too, primarily is a consequence of the need to operate the reactor in a plug-flow mode.

Fourth, the immobilized microbe reactor is operated continuously in a plug-flow mode. While expressly distinguishing the method of the present invention from a batch process, the use of the term "continuous" does not imply any minimum period of operation. The term "plug-flow" is synonymous with the term "packed bed". The term, of course, implies an absence of agitation within the column, either of the bed (in this case, the immobilized microbes) or the medium, although a degree of medium turbulence within the reactor may be unavoidable.

It should be apparent that medium composition, medium pH, medium flow rate, column dimensions, column or immobilized microbe temperature, and like factors all are dependent, at least in part, on the particular microbe species to be employed and the desired process parameters and goals. Thus, such factors can be determined readily by those skilled in the art and, hence, are not critical to the present invention.

Because of the wide-spread use of the chemostat and turbidostat, it should be apparent that the use of immobilized microbes in such devices as described herein represents a particular specific embodiment of the present invention. While the construction and use of the chemostat or turbidostat need not be altered significantly in order to utilize immobilized microbes as the microbe-producing culture, the use of immobilized microbes will eliminate wash-out and the problems associated therewith.

The present invention is further illustrated, but not limited, by the examples which follow. Those parameters or conditions which are common to all or most of the examples are discussed first, however. In every case, the immobilized microbes were essentially covered with medium. Furthermore, it was readily determined that, in most instances, the microbes in the examples were substantially in a logarithmic growth phase. Such determination was made by plotting the total number of microbes generated versus the total hours, i.e., the number of hours after a rate change. For example, the table below summarizes the data points for a flow rate of 138 ml./hr. with a *Bacillus subtilis* microbial generator (see Table 1, First Trial, infra):

| Count Cfu/ml[a] | Flow Rate ml./hr. | Count Cfu/hr.[b] | Hours After Rate Change | Total Count[c] | Cum. Total Count[d] |
|---|---|---|---|---|---|
| $7.4 \times 10^6$ | 138 | $1.0 \times 10^9$ | 8.0 | $8.2 \times 10^9$ | $8.2 \times 10^9$ |
| $8.4 \times 10^6$ | 138 | $1.2 \times 10^9$ | 10.5 | $2.9 \times 10^9$ | $1.1 \times 10^{10}$ |
| $1.2 \times 10^7$ | 138 | $1.7 \times 10^9$ | 12.0 | $2.5 \times 10^9$ | $1.3 \times 10^{10}$ |
| $1.8 \times 10^6$ | 138 | $2.5 \times 10^8$ | 16.0 | $9.9 \times 10^8$ | $1.4 \times 10^{10}$ |

[a] By plate count, expressed as colony forming units (cfu).
[b] The product of column 1 times column 3.
[c] The product of column 3 times the number of hours since the last sampling, i.e., 8.0, 2.5, 1.5, and 4 hours, respectively, for each of the four samplings.
[d] The cumulative sum of the total counts of column 5.

By plotting the values in column six on semilogarithmic graph paper versus hours after rate change (column 4), it is readily apparent that, under the conditions of the experiment, the immobilized microbes are substantially in a logarithmic growth state. Similar evaluations can be carried out for the other data in the examples.

MATERIALS AND METHODS

A. Columns

Fischer and Porter 150×9 mm glass chromatographic columns were employed (Fischer and Porter Co., Warminster, Penn.). At the bottom of each column a nylon grid or screen was located to support the immobilized microbes. Media were steam sterilized in 8- to 20-l bottles containing Tygon delivery tubes. Each delivery tube was attached to an Isco Model 310 metering pump (Instrumentation Specialties Co., Lincoln; Nebraska). A second, sterilized Tygon tube connected the pump to the column. No provision for oxygenation, other than that dissolved in the original medium, was made. The effluent from each column was monitored for the presence of microbial cells. Each column was operated continuously in a plug-flow mode.

B. Estimation of Cell Numbers

1. Plate Count

Each sample to be examined was serially diluted in decimal series. One ml. of each dilution was transferred by sterile pipette to sterile petri dishes. To each dish was added approximately 15 ml. of nutrient agar which had been melted and cooled to about 50° C. The contents of each dish then were mixed by gently rotating the dish. After the agar had solidified, each culture plate was incubated for 24 hours and examined for the presence of colonies.

The plate count is based on the assumption that each bacterium trapped in or on nutrient agar medium will multiply and produce a visible colony. Thus, each colony theroetically represents the progeny of a single cell present in the original inoculum. The plate count, however, is subject to error since the cells of many types of microbes will stick or clump together, thereby giving rise to but a single colony. Hence, the plate count provides what amounts to a minimum cell count with the possible error being as great as about ten percent.

2. Estimation of ATP

A sample of column effluent was filtered through a microporous membrane which retains microbial cells. The cellular ATP (adenosine 5'-triphosphate) then was thoroughly extracted with dimethylsulfoxide (DMSO). The extracted cells were washed several times with aqueous buffer and the washings were combined with the DMSO extract. An aliquot of the combined solutions was injected into the cuvette of a DuPont Model 760 Biometer, which cuvette contains luciferin and luciferase. The resulting chemiluminescence was measured by the instrument which had been calibrated to read either the quantity of ATP or the number of cells. Calibration was carried out by injecting into the cuvette a solution containing a known amount of ATP. For additional information regarding the Biometer and its use, see Instruction Manual, 760 Luminescence Biometer, E. I. DuPont de Nemours & Co., Instrument Products Division, Wilmington, Del., December 1970.

Cell counts by assay of ATP is based on the presumption that each microbial cell contains a small but definite or constant amount of ATP. The amount of microbial ATP does not change during the various phases of microbial growth, but is destroyed upon the death of the cell. Thus, the ATP assay provides a means of estimating the number of viable microbial cells in a sample.

EXAMPLE 1

Bacillus subtilis Microbial Generator

About 1 g. of a porous cordierite inorganic support, 18–25 mesh, U.S. Standard Sieve, having an average pore diameter of 4.5, was placed in a 10-ml. Erlenmeyer flask. To the flask then was added 6 ml. of an acetone solution containing 0.5% by volume of PAPI-901 (Upjohn Company, Polymer Chemical Division, Kalamazoo, Michigan), a polymeric isocyanate comprising phenyl isocyanate moieties separated by methylene groups. The resulting mixture was agitated (shaken) for 45 min. in a water bath at 22° C. The acetone solution then was decanted from the support. To the support then was added about 5 ml. of a suspension of *Bacillus subtilis* in 0.1 M phosphate buffer, pH 7.2. The mixture was returned to the water bath and shaken overnight (about 18 hours) at 22° C. The microbial suspension was decanted from the inorganic support which was washed with three 10-ml. portions of buffer. Ten ml. of buffer then was added to the flask and the support was again shaken at 22° C. for about five hours. The buffer was decanted from the support which then was placed in a 150×9 mm. column.

Medium was pumped downwardly through the column and immobilized microbes at ambient temperature, exiting at the bottom of the column. The medium was Bushnell-Haas medium containing sodium caseinate. Thus, the medium contained the following, per liter of medium: 1 g. sodium caseinate, 1 g. ammonium nitrate, 1 g. potassium monohydrogen phosphate, 1 g. potassium dihydrogen phosphate, 0.2 g. magnesium sulfate, 0.02 g. calcium chloride, and two drops of a saturated aqueous solution of ferric chloride. The medium pH was adjusted to 7.2 with aqueous sodium hydroxide.

Three trials were conducted, with the second and third trials being directed to a study of the effect of high flow rates. The results of these trials are summarized in Table I.

TABLE I

*Bacillus subtilis* Microbial Generator

| No. Hours After: | | Flow Rate, | Bacterial Count, cfu[a] | |
|---|---|---|---|---|
| Start | Rate Change | ml./hr. | per ml. | per hr. |
| 2.0 | 2.0 | 60 | $1.4 \times 10^4$ | $8.4 \times 10^5$ |
| 4.5 | 4.5 | 60 | $2.4 \times 10^4$ | $1.4 \times 10^6$ |
| 19.5 | 19.5 | 72[b] | $9.0 \times 10^5$ | $6.5 \times 10^7$ |
| 22.5 | 22.5 | 72 | $2.2 \times 10^6$ | $1.6 \times 10^8$ |
| 25.0 | 25.0 | 72 | $1.0 \times 10^7$ | $7.2 \times 10^8$ |
| 28.5 | 28.5 | 72 | $3.7 \times 10^6$ | $2.7 \times 10^8$ |
| 44.0 | 8.0 | 138 | $7.4 \times 10^6$ | $1.0 \times 10^9$ |
| 46.5 | 10.5 | 138 | $8.4 \times 10^6$ | $1.2 \times 10^9$ |
| 49.0 | 12.0 | 138 | $1.2 \times 10^7$ | $1.7 \times 10^9$ |
| 53.0 | 16.0 | 138 | $1.8 \times 10^6$ | $2.5 \times 10^8$ |
| Second Trial | | | | |
| 5.0 | 5.0 | 120 | $2.5 \times 10^5$ | $3.0 \times 10^7$ |
| 21.0 | 21.0 | 120 | $2.2 \times 10^5$ | $2.6 \times 10^7$ |
| 24.5 | 3.0 | 240 | $8.5 \times 10^5$ | $2.0 \times 10^8$ |
| 52.0 | 31.0 | 240 | $3.3 \times 10^6$ | $7.9 \times 10^8$ |
| 69.0 | 48.0 | 240 | $9.6 \times 10^6$ | $2.3 \times 10^9$ |
| 76.5 | 7.5 | 500 | $3.2 \times 10^6$ | $1.6 \times 10^9$ |
| 92.5 | 2.0 | 1000 | $5.6 \times 10^6$ | $5.6 \times 10^9$ |
| 94.5 | 4.0 | 1000 | $3.6 \times 10^6$ | $3.6 \times 10^9$ |
| 97.5 | 1.0 | 2500 | $1.8 \times 10^5$ | $4.5 \times 10^8$ |
| 99.5 | 3.0 | 2500 | $4.0 \times 10^5$ | $1.0 \times 10^9$ |
| 101.5 | 5.0 | 2500 | $3.8 \times 10^6$ | $9.5 \times 10^9$ |
| 106.5 | 10.0 | 2500 | $1.6 \times 10^7$ | $3.9 \times 10^{10}$ |
| Third Trial | | | | |
| 0.5 | 0.5 | 250 | $6.0 \times 10^3$ | $1.5 \times 10^6$ |
| 3.5 | 3.5 | 250 | $3.0 \times 10^5$ | $7.5 \times 10^7$ |
| 15.5 | 12.0 | 500 | $5.1 \times 10^6$ | $2.6 \times 10^9$ |
| 21.0 | 16.5 | 500 | $2.5 \times 10^6$ | $1.2 \times 10^9$ |
| 24.0 | 19.5 | 500 | $2.5 \times 10^6$ | $1.2 \times 10^9$ |
| 28.0 | 23.5 | 500 | $2.5 \times 10^6$ | $1.2 \times 10^9$ |
| 32.0 | 27.5 | 500 | $9.0 \times 10^7$ | $4.5 \times 10^{10}$ |
| 40.0 | 8.0 | 1000 | $8.0 \times 10^7$ | $8.0 \times 10^{10}$ |
| 41.0 | 9.0 | 1000 | $5.0 \times 10^7$ | $5.0 \times 10^{10}$ |
| 48.5 | 16.5 | 1000 | $5.0 \times 10^7$ | $5.0 \times 10^{10}$ |
| 66.0 | 33.0 | 1000 | $1.1 \times 10^7$ | $1.1 \times 10^{10}$ |

TABLE I-continued

*Bacillus subtilis* Microbial Generator

| No. Hours After: | | Flow Rate, | Bacterial Count, cfu[a] | |
|---|---|---|---|---|
| Start | Rate Change | ml./hr. | per ml. | per hr. |
| 73.25 | 7.25 | 2500 | $4.9 \times 10^7$ | $1.2 \times 10^{11}$ |
| 100.0 | 33.0 | 1280 | $1.0 \times 10^7$ | $1.3 \times 10^{10}$ |
| 102.5 | 35.5 | 1280 | $9.0 \times 10^7$ | $1.2 \times 10^{11}$ |
| 125.0 | 58.0 | 1280 | $3.0 \times 10^7$ | $3.8 \times 10^{10}$ |

[a] by plate count, expressed as colony forming units (cfu).
[b] Rate change was fortuitous, resulting solely from an apparent internal adjustment within the pump.

EXAMPLE 2

Flavobacterium sp. Microbial Generator

The procedure of Example 1 was repeated, except that Flavobacterium sp. was employed in place of *Bacillus subtilis*. Table II summarizes the data obtained. To determine the effects of storage on immobilized microbes employed in a microbial generator, the column used to obtain the data in Table II was drained, washed by shaking with fresh medium, drained again, filled with fresh medium, and stored at 6° C. for one week. The column then was reused. The data obtained upon reuse after storage are summarized in Table III.

TABLE II

*Flavobacterium sp.* Microbial Generator

| No. Hours After: | | Flow Rate, | Bacterial Count, cfu[a] | |
|---|---|---|---|---|
| Start | Rate Change | ml./hr. | per ml. | per hr. |
| 0 | 0 | 25 | 0 | 0 |
| 2.0 | 1.0 | 100 | $6.0 \times 10^4$ | $6.0 \times 10^6$ |
| 19.0 | 18.0 | 100 | $5.0 \times 10^6$ | $5.0 \times 10^8$ |
| 20.5 | 19.5 | 100 | $3.0 \times 10^6$ | $3.0 \times 10^8$ |
| 23.0 | 22.0 | 100 | $8.0 \times 10^6$ | $8.0 \times 10^8$ |
| 26.0 | 0.0 | 250 | $3.4 \times 10^7$ | $8.5 \times 10^9$ |
| 27.0 | 1.0 | 250 | $2.2 \times 10^7$ | $5.5 \times 10^9$ |
| 42.0 | 16.0 | 250 | $4.9 \times 10^7$ | $1.2 \times 10^{10}$ |
| 47.5 | 5.5 | 500 | $3.7 \times 10^7$ | $1.8 \times 10^{10}$ |
| 51.0 | 9.0 | 500 | $3.8 \times 10^7$ | $1.9 \times 10^{10}$ |
| 66.0 | 21.0 | 500 | $4.4 \times 10^7$ | $2.2 \times 10^{10}$ |
| 68.0 | 1.0 | 1000 | $1.0 \times 10^7$ | $1.0 \times 10^{10}$ |
| 70.0 | 2.0 | 1000 | $1.7 \times 10^7$ | $1.7 \times 10^{10}$ |
| 72.0 | 4.0 | 1000 | $1.3 \times 10^7$ | $1.3 \times 10^{10}$ |
| 75.0 | 7.0 | 1000 | $1.0 \times 10^7$ | $1.0 \times 10^{10}$ |
| 80.0 | 12.0 | 1000 | $8.0 \times 10^6$ | $8.0 \times 10^9$ |
| 90.0 | 22.0 | 1000 | $9.0 \times 10^6$ | $9.0 \times 10^9$ |
| 95.0 | 27.0 | 1000 | $6.0 \times 10^6$ | $6.0 \times 10^9$ |
| 97.5 | 29.5 | 1000 | $7.0 \times 10^6$ | $7.0 \times 10^9$ |

[a] by plate count, expressed as colony forming units (cfu).

TABLE III

*Flavobacterium sp.* Microbial Generator With Previously-Used Stored Column

| No. Hours After: | | Flow Rate, | Bacterial Count, cfu[a] | |
|---|---|---|---|---|
| Start | Rate Change | ml./hr. | per ml. | per hr. |
| 0 | 0 | 100 | — | — |
| 1.5 | 1.5 | 100 | $1.0 \times 10^4$ | $1.0 \times 10^6$ |
| 17.5 | 17.5 | 100 | $3.0 \times 10^4$ | $3.0 \times 10^6$ |
| 20.5 | 20.5 | 100 | $3.0 \times 10^4$ | $3.0 \times 10^6$ |
| 22.5 | 22.5 | 100 | $2.0 \times 10^5$ | $2.0 \times 10^7$ |
| 26.0 | 26.0 | 100 | $1.8 \times 10^7$ | $1.8 \times 10^9$ |
| 28.5 | 28.5 | 100 | $1.4 \times 10^7$ | $1.4 \times 10^9$ |
| 41.0 | 41.0 | 100 | $3.0 \times 10^6$ | $3.0 \times 10^8$ |
| 41.3 | 0.3 | 250 | $3.0 \times 10^6$ | $7.5 \times 10^8$ |
| 43.0 | 2.0 | 250 | $8.0 \times 10^6$ | $2.0 \times 10^9$ |
| 43.5 | 2.5 | 250 | $5.0 \times 10^6$ | $1.2 \times 10^9$ |
| 44.0 | 3.0 | 250 | $5.0 \times 10^6$ | $1.2 \times 10^9$ |
| 44.5 | 3.5 | 250 | $1.5 \times 10^7$ | $4.5 \ 1.8 \ 10^9$ |
| 45.0 | 4.0 | 250 | $2.0 \times 10^7$ | $5.0 \times 10^9$ |
| 45.5 | 4.5 | 250 | $2.2 \times 10^7$ | $5.5 \times 10^9$ |
| 46.0 | 5.0 | 250 | $1.9 \times 10^7$ | $4.8 \times 10^9$ |
| 46.5 | 5.5 | 250 | $1.2 \times 10^8$ | $3.0 \times 10^{10}$ |
| 47.0 | 0.5 | 500 | $8.5 \times 10^7$ | $4.2 \times 10^{10}$ |

TABLE III-continued

*Flavobacterium sp.* Microbial Generator With Previously-Used Stored Column

| No. Hours After: | | Flow Rate, | Bacterial Count, cfu[a] | |
|---|---|---|---|---|
| Start | Rate Change | ml./hr. | per ml. | per hr. |
| 47.5 | 1.5 | 500 | $1.1 \times 10^8$ | $5.5 \times 10^{10}$ |
| 48.0 | 2.0 | 500 | $5.8 \times 10^7$ | $2.9 \times 10^{10}$ |
| 48.5 | 2.5 | 500 | $2.8 \times 10^7$ | $1.4 \times 10^{10}$ |
| 49.0 | 3.0 | 500 | $1.7 \times 10^7$ | $8.5 \times 10^9$ |
| 49.5 | 3.5 | 500 | $5.1 \times 10^7$ | $2.6 \times 10^{10}$ |
| 52.5 | 6.5 | 500 | $8.0 \times 10^7$ | $4.0 \times 10^{10}$ |
| 53.5 | 7.5 | 500 | $1.8 \times 10^7$ | $9.0 \times 10^9$ |
| 57.0 | 11.0 | 500 | $1.7 \times 10^7$ | $8.5 \times 10^9$ |

[a] by plate count, expressed as colony forming units (cfu).

EXAMPLE 3

*Escherichia coli* Microbial Generator

The procedure of Example 1 was repeated, except that *Escherichia coli* K12 was employed in place of *Bacillus subtilis* and the caseinate-containing Bushnell-Haas medium was replaced with a medium containing 10 g. of lactose and 4 g. of Difco Nutrient Broth (Difco Laboratories, Detroit, Mich.) per liter of medium. The data are presented in Table IV. To evaluate the effect of a minimal medium on microbe production, the procedure was repeated, using Bushnell-Haas medium containing 0.1% weight per volume lactose. Toward the end of the trial, the nutrient value of the medium was enhanced by the addition of glucose at a level of 1% weight per volume. Table V summarizes the effect of the minimal medium on microbial cell production. Two additional trials were conducted to evaluate the effect of very high flow rates; to achieve flow rates greater than 2500 ml./hr., the Isco Model 310 pump was replaced with a Masterflex peristaltic pump (Cole-Parmer Instrument Co., Chicago, Ill.). In both of these trials the medium was nutrient broth (4 g./l). The data from these two additional trials are summarized in Tables VI and VII, respectively.

TABLE IV

*Escherichia coli* K12 Microbial Generator

| No. Hours After: | | Flow Rate, | Bacterial Count, cfu[a] | |
|---|---|---|---|---|
| Start | Rate Change | ml./hr. | per ml. | per hr. |
| 0 | 0 | 25 | 0 | 0 |
| 1.5 | 1.5 | 25 | $2.0 \times 10^6$ | $5.0 \times 10^7$ |
| 2.25 | 2.25 | 25 | $2.0 \times 10^6$ | $5.0 \times 10^7$ |
| 5.0 | 5.0 | 25 | $4.0 \times 10^6$ | $1.0 \times 10^8$ |
| 17.5 | 12.5 | 10 | $1.2 \times 10^7$ | $1.2 \times 10^8$ |
| 20.0 | 2.0 | 25 | $1.3 \times 10^7$ | $3.2 \times 10^8$ |
| 22.0 | 4.0 | 25 | $5.1 \times 10^7$ | $1.3 \times 10^9$ |
| 24.5 | 1.5 | 100 | $1.7 \times 10^7$ | $1.7 \times 10^9$ |
| 26.5 | 3.5 | 100 | $1.6 \times 10^7$ | $1.6 \times 10^9$ |
| 42.0 | 20.0 | 100 | $3.9 \times 10^7$ | $3.9 \times 10^9$ |
| 44.5 | 2.5 | 250 | $3.0 \times 10^7$ | $7.5 \times 10^9$ |
| 45.5 | 3.5 | 250 | $1.6 \times 10^7$ | $4.0 \times 10^9$ |
| 46.5 | 4.5 | 250 | $2.8 \times 10^7$ | $7.0 \times 10^9$ |
| 66.0 | 10.0 | 500 | $4.7 \times 10^7$ | $2.4 \times 10^{10}$ |
| 68.5 | 12.5 | 500 | $3.8 \times 10^7$ | $1.9 \times 10^{10}$ |
| 71.0 | 1.5 | 1000 | $4.5 \times 10^7$ | $4.5 \times 10^{10}$ |
| 72.0 | 2.5 | 1000 | $3.0 \times 10^8$ | $3.0 \times 10^{11}$ |
| 73.0 | 3.5 | 1000 | $2.9 \times 10^8$ | $2.9 \times 10^{11}$ |
| 73.5 | 4.0 | 1000 | $6.0 \times 10^7$ | $6.0 \times 10^{10}$ |
| 74.0 | 4.5 | 1000 | $2.5 \times 10^7$ | $2.5 \times 10^{10}$ |
| 74.5 | 5.0 | 1000 | $1.5 \times 10^7$ | $1.5 \times 10^{10}$ |
| 76.0 | 5.5 | 1000 | $1.0 \times 10^7$ | $1.0 \times 10^{10}$ |

[a] by plate count, expressed as colony forming units (cfu).

TABLE V

*Escherichia coli* K12 Microbial Generator With A Minimal Medium

| No. Hours After: Start | Rate Change | Flow Rate, ml./hr. | Bacterial Count, cfu[a] per ml. | per hr. |
|---|---|---|---|---|
| 0.5 | .33 | 50 | $1.5 \times 10^7$ | $7.5 \times 10^8$ |
| 2.0 | 1.8 | 50 | $1.1 \times 10^7$ | $5.5 \times 10^8$ |
| 2.1 | .12 | 100 | $6.8 \times 10^6$ | $6.8 \times 10^8$ |
| 2.25 | .25 | 100 | $6.0 \times 10^6$ | $6.0 \times 10^8$ |
| 2.33 | .33 | 100 | $4.2 \times 10^6$ | $4.2 \times 10^8$ |
| 2.5 | .5 | 100 | $4.0 \times 10^6$ | $4.0 \times 10^8$ |
| 2.75 | .75 | 100 | $8.6 \times 10^7$ | $8.6 \times 10^9$ |
| 3.0 | 1.0 | 100 | $6.3 \times 10^7$ | $3.6 \times 10^9$ |
| 3.5 | 1.5 | 100 | $8.0 \times 10^6$ | $8.0 \times 10^8$ |
| 4.0 | 2.0 | 100 | $2.0 \times 10^6$ | $2.0 \times 10^8$ |
| 5.0 | 3.0 | 100 | $8.0 \times 10^6$ | $8.0 \times 10^8$ |
| 6.5 | 4.5 | 100 | $9.1 \times 10^6$ | $9.1 \times 10^8$ |
| 14.5 | 12.5 | 100 | $6.0 \times 10^6$ | $6.0 \times 10^8$ |
| 18.0 | 16.0 | 100 | $8.0 \times 10^6$ | $8.0 \times 10^8$ |
| 18.5 | 16.5 | 50 | $2.8 \times 10^7$ | $1.4 \times 10^9$ |
| 19.0 | 17.0 | 50 | $1.4 \times 10^7$ | $7.0 \times 10^8$ |
| 19.16 | .16 | 25 | $1.8 \times 10^8$ | $4.5 \times 10^9$ |
| 20.25 | 1.25 | 25 | $4.4 \times 10^7$ | $1.1 \times 10^9$ |
| 21.5 | 20.0 | 25 | $3.0 \times 10^7$ | $7.5 \times 10^8$ |
| 23.5 | 2.0 | 12.5 | $7.5 \times 10^7$ | $9.4 \times 10^8$ |
| 24.5 | 1.0 | 50 | $1.2 \times 10^7$ | $6.0 \times 10^8$ |
| 25.5 | 1.0 | 50[b] | $8.1 \times 10^8$ | $4.0 \times 10^{10}$ |
| 28.0 | .5 | 100 | $6.0 \times 10^6$ | $6.0 \times 10^8$ |

[a] by plate count, expressed as colony forming units (cfu).
[b] Use of glucose-containing medium started.

TABLE VI

High Flow Rate *Escherichia coli* K12 Microbial Generator: First Trial

| No. Hours After: Start | Rate Change | Flow Rate, ml./hr. | Bacterial Count, cells[a] per ml. | per hr. |
|---|---|---|---|---|
| 0 | 0 | 100 | — | — |
| 0.25 | 0.25 | 100 | $4.9 \times 10^7$ | $4.9 \times 10^9$ |
| 15.5 | 15.5 | 100 | $1.3 \times 10^9$ | $1.3 \times 10^{11}$ |
| 16.5 | 1.0 | 250 | $7.2 \times 10^8$ | $1.8 \times 10^{11}$ |
| 17.0 | 1.5 | 250 | $1.5 \times 10^8$ | $3.8 \times 10^{10}$ |
| 18.0 | 1.0 | 500 | $1.9 \times 10^8$ | $9.5 \times 10^{10}$ |
| 19.0 | 1.0 | 1000 | $6.1 \times 10^8$ | $6.1 \times 10^{11}$ |
| 20.25 | 1.25 | 2500 | $4.1 \times 10^8$ | $1.0 \times 10^{12}$ |
| 21.0 | 2.0 | 2500 | $1.9 \times 10^8$ | $4.8 \times 10^{11}$ |
| 22.0 | 3.0 | 2500 | $1.1 \times 10^9$ | $2.8 \times 10^{12}$ |
| 23.0 | 4.0 | 2500 | $1.7 \times 10^8$ | $4.2 \times 10^{12}$ |
| 24.0 | 0.5 | 4200 | $4.0 \times 10^6$ | $1.7 \times 10^{10}$ |
| 25.0 | 1.5 | 4200 | $1.8 \times 10^7$ | $7.6 \times 10^{10}$ |
| 26.0 | 2.5 | 4200 | $4.2 \times 10^7$ | $1.8 \times 10^{11}$ |
| 27.0 | 3.5 | 4200 | $4.6 \times 10^7$ | $1.9 \times 10^{11}$ |
| 28.0 | 0.5 | 7680 | $5.2 \times 10^7$ | $4.0 \times 10^{11}$ |
| 29.0 | 1.5 | 7680 | $4.4 \times 10^6$ | $3.4 \times 10^{10}$ |
| 30.0 | 2.5 | 7680 | $3.7 \times 10^7$ | $2.8 \times 10^{11}$ |
| 31.0 | 3.5 | 7680 | $1.4 \times 10^7$ | $1.1 \times 10^{11}$ |
| 32.0 | 4.5 | 7826 | $9.7 \times 10^6$ | $7.6 \times 10^{10}$ |
| 33.0 | 5.5 | 7826 | $5.4 \times 10^6$ | $4.2 \times 10^{10}$ |
| 34.0 | 0.5 | 13333 | $7.3 \times 10^6$ | $9.7 \times 10^{10}$ |
| 35.0 | 1.5 | 13333 | $7.0 \times 10^6$ | $9.3 \times 10^{10}$ |
| 36.0 | 2.5 | 13333 | $2.8 \times 10^7$ | $3.7 \times 10^{11}$ |
| 37.0 | 3.5 | 13333 | $7.2 \times 10^7$ | $9.6 \times 10^{11}$ |
| 38.0 | 1.0 | 18947 | $1.3 \times 10^7$ | $2.5 \times 10^{11}$ |
| 39.0 | 2.0 | 18947 | $5.3 \times 10^6$ | $1.0 \times 10^{11}$ |
| 40.0 | 1.0 | 23000 | $2.2 \times 10^7$ | $5.1 \times 10^{11}$ |
| 41.0 | 2.0 | 23000 | $8.4 \times 10^6$ | $1.9 \times 10^{11}$ |
| 42.0 | 3.0 | 23000 | $2.5 \times 10^7$ | $5.8 \times 10^{11}$ |
| 43.0 | 4.0 | 23000 | $5.3 \times 10^6$ | $1.2 \times 10^{11}$ |

[a] by ATP assay.

TABLE VII

High Flow Rate *Escherichia coli* K12 Microbial Generator: Second Trial

| No. Hours After: Start | Rate Change | Flow Rate, ml./hr. | Bacterial Count, cells[a] per ml. | per hr. |
|---|---|---|---|---|
| 0 | 0 | 100 | 0 | 0 |
| 15.0 | 15.0 | 100 | $2.4 \times 10^8$ | $2.4 \times 10^{10}$ |
| 16.0 | 1.0 | 250 | $4.9 \times 10^7$ | $1.2 \times 10^{10}$ |
| 17.0 | 2.0 | 250 | $2.9 \times 10^8$ | $7.2 \times 10^{10}$ |
| 17.5 | 0.5 | 500 | $1.5 \times 10^8$ | $7.5 \times 10^{10}$ |
| 18.0 | 1.0 | 500 | $1.1 \times 10^8$ | $5.5 \times 10^{10}$ |
| 18.5 | 0.5 | 1000 | $8.7 \times 10^7$ | $8.7 \times 10^{10}$ |
| 19.0 | 1.0 | 1000 | $1.3 \times 10^8$ | $1.3 \times 10^{11}$ |
| 20.0 | 2.0 | 1000 | $2.3 \times 10^8$ | $2.3 \times 10^{11}$ |
| 20.5 | 2.5 | 1000 | $2.8 \times 10^8$ | $2.8 \times 10^{11}$ |
| 21.0 | 3.0 | 1000 | $2.7 \times 10^8$ | $2.7 \times 10^{11}$ |
| 21.5 | 3.5 | 1000 | $2.6 \times 10^8$ | $2.6 \times 10^{11}$ |
| 22.0 | 0.5 | 2500 | $4.7 \times 10^7$ | $1.2 \times 10^{11}$ |
| 22.5 | 1.0 | 2500 | $8.6 \times 10^7$ | $2.2 \times 10^{11}$ |
| 23.0 | 1.5 | 2500 | $1.3 \times 10^8$ | $3.2 \times 10^{11}$ |
| 23.5 | 2.0 | 2500 | $1.1 \times 10^8$ | $3.2 \times 10^{11}$ |
| 24.0 | 2.5 | 2500 | $4.9 \times 10^8$ | $1.2 \times 10^{12}$ |
| 26.0 | 1.0 | 5040 | $2.8 \times 10^7$ | $1.4 \times 10^{11}$ |
| 27.0 | 2.0 | 5040 | $2.7 \times 10^7$ | $1.4 \times 10^{11}$ |
| 28.0 | 3.0 | 5040 | $3.4 \times 10^8$ | $1.7 \times 10^{12}$ |
| 30.0 | 1.0 | 7560 | $3.2 \times 10^7$ | $2.4 \times 10^{11}$ |
| 31.0 | 2.0 | 7560 | $3.2 \times 10^7$ | $2.4 \times 10^{11}$ |
| 32.0 | 3.0 | 7560 | $1.1 \times 10^8$ | $8.3 \times 10^{11}$ |
| 33.0 | 4.0 | 7560 | $9.8 \times 10^7$ | $7.4 \times 10^{11}$ |
| 34.0 | 1.0 | 12413 | $2.0 \times 10^5$ | $2.5 \times 10^9$ |
| 35.0 | 2.0 | 12413 | $1.9 \times 10^7$ | $2.4 \times 10^{11}$ |
| 36.0 | 1.0 | 22500 | $1.9 \times 10^7$ | $4.3 \times 10^{11}$ |
| 37.0 | 2.0 | 22500 | $1.4 \times 10^7$ | $3.2 \times 10^{11}$ |
| 38.0 | 1.0 | 18000 | $9.6 \times 10^6$ | $1.7 \times 10^{11}$ |
| 29.0 | 2.0 | 18000 | $2.0 \times 10^7$ | $3.6 \times 10^{11}$ |
| 40.3 | 3.3 | 18000 | $5.3 \times 10^7$ | $9.5 \times 10^{11}$ |
| 40.5 | 3.5 | 18000 | $4.1 \times 10^7$ | $7.4 \times 10^{11}$ |

[a] by ATP assay

EXAMPLE 4

*Clostridium butyricum* Microbial Generator

The procedure of Example 1 was repeated, except that *Clostridium butyricum* was employed in place of *Bacillus subtilis*, the column and medium were maintained in an atmosphere of nitrogen, and the oxygen-free medium had the following composition, weight per volume: 0.05% potassium monohydrogen phosphate, 0.05% potassium dihydrogen phosphate, 0.02% magnesium sulfate heptahydrate, 0.001% manganese sulfate heptahydrate, 2% glucose, 0.1% asparagine, 0.25% tryptone, and 0.0002% methylene blue as an oxygen indicator. The data are presented in Table VIII.

TABLE VIII

| *Clostridium butyricum* Microbial Generator | | | | | | |
|---|---|---|---|---|---|---|
| No. Hours After: | | Flow Rate, | Bacterial Count | | | |
| Start | Rate Change | ml./hr. | cfu/ml.[a] | cfu/hr.[a] | cells/ml.[b] | cells/hr.[b] |
| 0 | 0 | 5 | $2 \times 10^8$ | $1 \times 10^9$ | $1.2 \times 10^8$ | $6 \times 10^8$ |
| 24 | 24 | 5 | $3 \times 10^9$ | $1.5 \times 10^9$ | $4.5 \times 10^9$ | $2.2 \times 10^{10}$ |
| 28[c] | 4 | 25 | $1.2 \times 10^9$ | $3 \times 10^{10}$ | $4.2 \times 10^8$ | $1 \times 10^{10}$ |

TABLE VIII-continued

Clostridium butyricum Microbial Generator

| No. Hours After: Start | Flow Rate, Rate Change | ml./hr. | cfu/ml.[a] | Bacterial Count cfu/hr.[a] | cells/ml.[b] | cells/hr.[b] |
|---|---|---|---|---|---|---|
| 28.5[c] | 4.5 | 25 | $1.5 \times 10^9$ | $3.8 \times 10^{10}$ | $4.7 \times 10^8$ | $1.2 \times 10^{10}$ |

[a] by plate count, expressed as colony forming units (cfu).
[b] by ATP assay
[c] column contamination observed After about 28 hours of operation, a contaminant was observed on the column and subsequently was identified as a facultative anaerobe. The indicator present in the medium showed the absence of oxygen, however. Thus, even though the column was contaminated, the trial demonstrated that a microbial generator can operate successfully under anaerobic conditions.

EXAMPLE 5

Dilute Medium Microbial Generator Using *Escherichia Coli*

The procedure of Example 3 was repeated, except that the medium contained only 0.4 g./l. Difco nutrient broth. Throughout the trial, the flow rate was maintained at 250 ml./hr. The trial was terminated after 179 days because a contaminant in the column had become persistent and the inorganic support was being lost by abrasion. The results are presented in Table IX.

TABLE IX

Dilute Medium Microbial Generator Using *Escherichia coli* and a Flow Rate of 250 ml./hr.

| No. Days After Start | cfu/ml.[a] | cfu/hr.[a] | cells/ml.[b] | cells/hr.[b] |
|---|---|---|---|---|
| 1 | $4 \times 10^4$ | $1 \times 10^7$ | — | — |
| 8 | $2 \times 10^7$ | $5 \times 10^9$ | — | — |
| 10 | $2 \times 10^7$ | $5 \times 10^9$ | — | — |
| 23 | $4.5 \times 10^9$ | $1.1 \times 10^{12}$ | — | — |
| 50 | — | — | $3.7 \times 10^8$ | $9.2 \times 10^{10}$ |
| 79 | $1.6 \times 10^7$ | $4 \times 10^9$ | — | — |
| 91 | $1 \times 10^6$ | $2.5 \times 10^8$ | — | — |
| 148 | $2 \times 10^8$ | $5 \times 10^{10}$ | — | — |
| 155 | — | — | $1.3 \times 10^6$ | $3.2 \times 10^8$ |
| 179 | — | — | $5 \times 10^8$ | $1.2 \times 10^{11}$ |

[a] by plate count, expressed as colony forming units (cfu).
[b] by ATP assay.

EXAMPLE 6

*Saccharomyces cerevisiae* Microbial Generator

The procedure of Example 1 was repeated, except that *Saccharomyces cerevisiae* was employed in place of *Bacillus subtilis*, the inorganic support was a porous cordierite having pore diameters of from 5 to 60, and the medium used was Wildier's yeast medium having the following composition, weight per volume: 1.5% cane sugar, 2.5% magnesium sulfate, 2.5% potassium chloride, 2.5% ammonium chloride, 2.5% sodium monohydrogen phosphate, and 0.5% calcium carbonate, with the pH being adjusted to 5.0 with hydrochloric acid. The flow rate throughout the trial was 25 ml./hr. Table X presents the data obtained.

TABLE X

*Saccharomyces cerevisiae* Microbial Generator With a Flow Rate of 25 ml./hr.

| No. Hours After Start | Cell Count, cfu[a] per ml. | per hr. |
|---|---|---|
| 18[b] | $1 \times 10^6$ | $2.5 \times 10^7$ |
| 30[b] | $4.9 \times 10^6$ | $1.2 \times 10^8$ |

TABLE X-continued

*Saccharomyces cerevisiae* Microbial Generator With a Flow Rate of 25 ml./hr.

| No. Hours After Start | Cell Count, cfu[a] per ml. | per hr. |
|---|---|---|
| 48[b] | $9 \times 10^5$ | $2.2 \times 10^7$ |

[a] by plate count, expressed as colony forming units (cfu).
[b] The medium was contaminated by bacteria, so plate counts were obtained with highly-acidified agar so that only the yeast cells grew.

EXAMPLE 7

*Serratia marcescens* Microbial Generator

The procedure of Example 1 was repeated, except that *Serratia marcescens* was employed in place of *Bacillus subtilis* and the medium used was 50% Difco nutrient broth (4 g./l.). Two trials were conducted, the results being summarized in Table XI.

TABLE XI

*Serratia marcescens* Microbial Generator

| No. Hours After: Start | Flow Rate, Rate Change | ml./hr. | Bacterial Counts, cfu[a] per ml. | per hr. |
|---|---|---|---|---|
| First Trial ||||| 
| 0 | 0 | 100 | $5.0 \times 10^6$ | $5.0 \times 10^8$ |
| 0.5 | 0.5 | 100 | $4.0 \times 10^6$ | $4.0 \times 10^8$ |
| 1.0 | 0.5 | 250 | $7.0 \times 10^6$ | $1.8 \times 10^9$ |
| 1.5 | 0.5 | 500 | $2.0 \times 10^5$ | $1.0 \times 10^8$ |
| 2.0 | 0.5 | 1000 | $2.0 \times 10^4$ | $2.0 \times 10^7$ |
| 2.5 | 0.5 | 2500 | $2.0 \times 10^4$ | $5.0 \times 10^7$ |
| 3.0 | 1.0 | 2500 | $4.0 \times 10^4$ | $1.0 \times 10^8$ |
| Second Trial |||||
| 1.0 | 1.0 | 100 | $4.0 \times 10^6$ | $4.0 \times 10^8$ |
| 2.0 | 2.0 | 100 | $3.0 \times 10^7$ | $3.0 \times 10^9$ |
| 18.0 | 18.0 | 100 | $2.0 \times 10^7$ | $2.0 \times 10^9$ |
| 19.0 | 1.0 | 250 | $2.0 \times 10^7$ | $5.0 \times 10^9$ |
| 20.0 | 2.0 | 250 | $1.0 \times 10^7$ | $2.5 \times 10^{10}$ |
| 21.0 | 3.0 | 250 | $2.0 \times 10^7$ | $5.0 \times 10^9$ |
| 22.5 | 4.5 | 250 | $1.0 \times 10^6$ | $2.5 \times 10^8$ |
| 23.5 | 1.0 | 500 | $1.0 \times 10^7$ | $5.0 \times 10^9$ |
| 24.5 | 2.0 | 500 | $1.0 \times 10^7$ | $5.0 \times 10^9$ |
| 25.5 | 3.0 | 500 | $1.0 \times 10^7$ | $5.0 \times 10^9$ |
| 26.0 | 3.5 | 500 | $6.4 \times 10^{7b}$ | $3.2 \times 10^{10b}$ |
| 26.5 | 0.5 | 900 | $1.0 \times 10^7$ | $9.0 \times 10^9$ |

[a] by plate count, expressed as colony forming units (cfu).
[b] Cell count, determined by ATP assay.

EXAMPLE 8

*Neisseria gonorrhoeae* Microbial Generator

The organism, *Neisseria gonorrhoeae*, was obtained from the Center for Disease Control, Atlanta, Ga., and was designated as strain CDC F62. The immobilized microbe was prepared as follows: A suspension of the organism in GC broth containing 12% weight per volume sucrose was prepared such that the suspension had an optical density, at 660 nm, of 1.0. The sucrose-containing broth was prepared by mixing equal volumes of standard GC broth (described hereinafter) and 24% weight per volume aqueous sucrose solution. Two ml. of the suspension was added to 1 g. of the inorganic support described in Example 1. The resulting mixture was shaken at ambient temperature for three hours. Excess fluid was aspirated and the residue was placed in a dry ice-acetone bath for ten minutes. The frozen support then was maintained in a freeze-dryer (Virtis, Gardiner, N.Y.) overnight. The support then was stored at 4° C.

The column was as described hereinbefore, except that the column was obtained from Bio-Rad Laboratories, Richmond, California. The column was fitted at the top with a type N needle valve and at the bottom with a type D stopcock outlet. A glass water jacket was assembled around the outside of the column. Water at 35° C. was circulated through the jacket by a Haake water-bath pump (Polyscience Corp., Evanston, Ill.). The column was charged with immobilized microbe as already described.

The medium employed was GC broth which consisted of the same ingredients as GC medium base (Difco Laboratories, Detroit, Michigan) except that agar was omitted. To each liter of broth, 10 ml. of IsoVitaleX Enrichment (IVX, Baltimore Biological Laboratories, Cockeysville, Md.) or Kellogg's supplement (KS) [see R. W. Chandler et al., *J. Am. Vener. Dis. Assoc.*, 1, 14 (1974)] was added. VCN inhibitor (Baltimore Biological Laboratories) or the following antibiotic mixture (AM) also was incorporated into the medium: 30 µg./ml. vancomycin hydrochloride (Eli Lilly and Co., Indianapolis, Ind.), 7.5 µg/ml. sodium colistimethate (USP-NF Reference Standards, Inc., Rockville, Md.), 1.0 µg./ml. amphotericin B (USP-NF Reference Standards, Inc.), and 30 µg./ml. trimethoprim lactate (Burroughs Wellcome Company, Research Triangle Park, N.C.). As before, medium was supplied to the column by an Isco Model 310 pump.

Bacteria recovered from the column were presumptively identified as *N. gonorrhoeae* by colonial morphology and growth reactions on Thayer-Martin (TM) medium see J. D. Thayer and J. E. Martin, *Publ. Health Rep.* 81 559 (1966) as well as by oxidase and gram strain reactions. Identity confirmation was accomplished by sugar fermentation tests using Cysteine Tryptic Agar (Difco) to which 1% by weight lactose, sucrose, maltose, or dextrose was added. Standard plate counting procedures using GC broth and GC medium base (GCM) containing 1% by weight IVX were used to determine gonococcal concentrations (cfu/ml. or cfu/hr.) in the column effluent. The pump was sterilized by passing 70% isopropyl alcohol through the pump at 2500 ml./hr. for three hours, followed by flushing with 1500 ml. of sterile distilled water. The column, tubing, connectors, and medium all were autoclaved in accordance with accepted practice.

A first column was prepared, using 1 g. of immobilized microbe. The medium was passed through the column at 25 ml./hr.; the medium contained 1% IVX but no antibiotics. Effluent from the column was plated on GCM and TM medium at selected intervals. After 18 hours of operation, the column effluent yielded heavy mucous growth on GCM but no growth on TM medium. Oxidase tests and gram stain reactions (oxidase negative, gram-positive bacilli) were not characteristic of *N. gonorrhoeae*, indicating that the column and/or the medium had become contaminated. Thus, the column was discarded.

Consequently, a second column was prepared as before. The column was charged with 10 ml. of GC broth containing 1% IVX and allowed to stand overnight at 35° C. without passing medium through the column. After 15 hours, a sample of broth was withdrawn from the column and plated on GCM and TM medium and gram stained. GC broth containing 1% IVX and 1% VCN inhibitor then was started through the column at 25 ml./hr. During the sixth day of operation, the flow rate was increased to 100 ml./hr. During the eighth day, the IVX was replaced by KS, and during the ninth day the VCN inhibitor was replaced by AM. Samples were collected periodically and subjected to oxidase tests, sugar fermentation tests, gram stains, and plate counts. Operational data are summarized in Table XII, and Table XIII summarizes the results of the gonococci identification tests.

TABLE XII

*Neisseria gonorrhoeae* Microbial Generator
Summary of Operational Data

| After Start | Flow Rate, ml./hr. | No. Bacterial Count, cfu[a] per ml. | per hr. |
|---|---|---|---|
| 1 | 25 | $1.4 \times 10^8$ | $3.5 \times 10^9$ |
| 2 | 25 | | |
| 3 | 25 | | |
| 4 | 25 | | |
| 5 | 25 | $9 \times 10^7$ | $2.2 \times 10^9$ |
| 6 | 100[b] | $4.4 \times 10^{6c}$ | $4.4 \times 10^{8c}$ |
| 7 | 100 | $2.6 \times 10^8$ | $2.6 \times 10^{10}$ |
| 8 | 100 | | |
| 9 | 100 | $3.2 \times 10^8$ | $3.2 \times 10^{10}$ |
| 10 | 100 | | |
| 11 | 100 | | |
| 12 | 100 | $6.9 \times 10^7$ | $6.9 \times 10^{10}$ |

[a]by plate count, expressed as colony forming units. (cfu).
[b]Flow rate increased to 100 ml./hr. at 1:00 P.M.
[c]Average of four samples taken every two hours from 2:00 P.M. to 8.00 P.M.

TABLE XIII

*Neisseria gonorrhoeae* Microbial Generator
Summary of Gonococci Identification Tests

| No. Days After Start | Growth on[a] GCM | TM | Gram Stain | Oxidase Reaction | Fermentation[b] of D | M | S | L |
|---|---|---|---|---|---|---|---|---|
| 0 | + | + | GNDC[c] | + | | | | |
| 1 | + | + | GNDC | + | + | − | − | − |
| 2 | + | + | GNDC | + | + | | GNDC | + |
| 4 | + | + | GNDC | + | | | | |
| 5 | + | + | GNDC | + | + | − | − | − |
| 6 | + | + | GNDC | + | | | | |
| 7 | + | + | GNDC | + | | | | |
| 8 | + | + | GNDC | + | | | | |
| 9 | + | + | GNDC | + | | | | |
| 12 | + | + | GNDC | + | | | | |

[a]GCM = GC medium; TM = Thayer-Martin medium; and + = growth
[b]D = dextrose, M = maltose, S = sucrose, and L = lactose
[c]GNDC = gram-negative diplococci

What is claimed is:

1. A method for the continuous culturing of microbes in a plug-flow reactor which comprises the steps of:
   A. supplying medium to microbes immobilized on a porous inorganic support at a rate sufficient to maintain such microbes substantially in a logarithmic growth state and
   B. removing microbe-containing effluent from the immobilized microbes at a rate equal to the medium supply rate, wherein the microbes are selected from the group consisting of bacteria, yeasts, and fungus-like organisms; such reactor is operated continuously in a substantially plug-flow mode; the immobilized microbes are substantially covered by said medium; and such porous inorganic support has a controlled porosity such that at least 70% of the pores, on a pore size distribution basis, have a pore diameter,
- a. in the case of bacteria, at least as large as the smallest major dimension of the microbes but less than about five times the largest major dimension of the microbes;
- b. in the case of yeasts, at least as large as the smallest dimension of the microbes but less than about four times the largest dimension of the microbes; and
- c. in the case of fungus-like organisms, at least as large as the smallest major dimension of the microbes but less than about sixteen times the largest major dimension of the microbes.

2. The method of claim 1 in which the immobilized microbes are contained in a columnar vessel.

3. The method of claim 2 in which the inorganic support is siliceous.

4. The method of claim 3 in which the inorganic support is a cordierite material.

5. The method of claim 4 in which the microbes consist of a single species.

6. The method of claim 5 in which the microbes are selected from the group consisting of bacteria and yeasts.

7. The method of claim 6 in which the microbes are bacteria.

8. The method of claim 7 in which the microbes are selected from the group consisting of *Bacillus subtilis*, Flavobacterium sp., *Escherichia coli, Clostridium butyricum,* and *Neisseria gonorrhoeae.*

9. The method of claim 6 in which the microbes are a yeast.

10. The method of claim 9 in which the microbes are *Saccharomyses cerevisiae.*

* * * * *